(12) United States Patent
Lee et al.

(10) Patent No.: US 6,714,809 B2
(45) Date of Patent: Mar. 30, 2004

(54) CONNECTOR AND GUIDEWIRE CONNECTABLE THERETO

(75) Inventors: Chris Lee, Tewksbury, MA (US); Christine McNamara, Chelmsford, MA (US); Ingmar Viohl, Milwaukee, WI (US)

(73) Assignee: Surgi-Vision, Inc., Chelmsford, MA (US)

( * ) Notice: Subject to any disclaimer, the term of this patent is extended or adjusted under 35 U.S.C. 154(b) by 0 days.

(21) Appl. No.: 09/990,878

(22) Filed: Nov. 20, 2001

(65) Prior Publication Data

US 2002/0161421 A1 Oct. 31, 2002

Related U.S. Application Data

(60) Provisional application No. 60/252,003, filed on Nov. 20, 2000.

(51) Int. Cl.[7] .............................. A61B 5/055
(52) U.S. Cl. ................ 600/423; 600/424; 600/585; 439/578
(58) Field of Search ................ 600/423, 424, 600/585; 607/116; 128/899; 439/578

(56) References Cited

U.S. PATENT DOCUMENTS

| 4,682,125 | A | | 7/1987 | Harrison et al. ............ 333/12 |
|---|---|---|---|---|
| 5,057,106 | A | * | 10/1991 | Kasevich et al. ............ 606/33 |
| 5,178,159 | A | * | 1/1993 | Christian .................... 600/585 |
| 5,324,311 | A | * | 6/1994 | Acken ......................... 607/37 |
| 5,445,155 | A | * | 8/1995 | Sieben ....................... 600/443 |
| 5,699,801 | A | | 12/1997 | Atalar et al. ............. 128/653.2 |
| 5,792,055 | A | | 8/1998 | McKinnon .................. 600/410 |
| 5,797,848 | A | * | 8/1998 | Marian et al. .............. 600/459 |
| 5,928,145 | A | | 7/1999 | Ocali et al. ................. 600/410 |
| 6,004,269 | A | | 12/1999 | Crowley et al. ............ 600/439 |
| 6,031,375 | A | | 2/2000 | Atalar et al. ............... 324/307 |
| 6,263,229 | B1 | | 7/2001 | Atalar et al. ............... 600/423 |
| 6,408,202 | B1 | | 6/2002 | Lima et al. ................. 600/423 |
| 2001/0056232 | A1 | | 12/2001 | Lardo et al. ............... 600/423 |

FOREIGN PATENT DOCUMENTS

| EP | 0 466 424 A1 | 1/1992 |
|---|---|---|
| EP | 0 557 127 A2 | 8/1993 |
| JP | 10165404 | 6/1998 |
| WO | WO 89/11311 | 11/1989 |
| WO | WO 00/64003 | 10/2000 |

OTHER PUBLICATIONS

PCT International Search Report for International Application No. PCT/US01/43295.

* cited by examiner

Primary Examiner—Francis J. Jaworski
Assistant Examiner—Barry Pass
(74) Attorney, Agent, or Firm—Foley & Hoag LLP

(57) ABSTRACT

Connector and guidewires connectable thereto are disclosed which enable for the connection of guidewires requiring electrical connection to an external electrical source. These guidewires may be used for MRI imaging and the external source could be an MRI scanner. An embodiment of a guidewire is provided with enables for easier connection through improved dimensions and mechanical strength at the proximal end. An embodiment of a connector is provided which can attach to any guidewire or coaxial cable. These connectors provide for desirable mechanical and electrical properties while still enabling catheters and other tools to be used in conjunction with guidewires and other cables.

94 Claims, 13 Drawing Sheets

CONNECTOR AND GUIDEWIRE CONNECTABLE THERETO

CROSS-REFERENCE TO RELATED APPLICATION

This application claims the benefit of U.S. Provisional Patent Application Ser. No. 60/252,003, filed Nov. 20, 2000. The entire disclosure of this application is herein incorporated by reference.

BACKGROUND

The subject matter generally relates to the field of electronic connectors, more particularly to electronic connectors for use with magnetic resonance imaging guidewires.

Many percutaneous intravascular procedures use a guidewire as an initial approach of accessing a particular vessel. Once the distal guidewire tip has been placed at the area of interest, a catheter is passed over the wire from the proximal end using it as a guide to track the catheter into that vessel. In order to allow the catheter to pass, the entire length of the guidewire generally needs to fit within the lumen of the catheter.

SUMMARY

The following discloses, among other things, connectors designed to receive coaxial cables, including magnetic resonance imaging (MRI) guidewires. The following also discloses guidewires designed for insertion into connectors.

In accordance with one exemplary embodiment, a connector may include an orifice for receiving an end of a guidewire; a channel communicating with the orifice and providing an insertion path for the end of the guidewire; a first contact that is at least partly exposed to the channel, and is sized and shaped to couple with an inner conductor contact of the guidewire; a second contact that is at least partly exposed to the channel, and is sized and shaped to couple with an outer conductor contact of the guidewire; an output terminal electrically coupled to the first and second contacts; and a fastener structured and positioned to hold the end of the guidewire within the channel. The first and second contacts may be sequentially disposed along the insertion path.

The connector may include an interface circuit electrically coupled to the first and second contacts. The connector may include a connection detector exposed to the channel. The connector may include a DC blocking circuit coupled to at least one of the first and second contacts.

In accordance with another exemplary embodiment, a guidewire may include an inner conductor; an outer conductor coaxially disposed about the inner conductor; a distal end adapted for insertion into a subject to receive MRI signals; and a proximal end adapted for insertion into a connector. The proximal end may have an outer conductor contact coupled electrically to the outer conductor, and an extended section of the inner conductor that extends axially beyond the outer conductor contact. The extended section may have an inner conductor contact and an insulated area interposed between the outer conductive contact and the inner conductive contact. The inner conductor contact may have an electrically conductive material disposed at least partially around the inner conductor. The insulated area may have an electrically insulating material disposed at least partially around the inner conductor. The guidewire may include an extension attachment coupled to the proximal end of the guidewire.

In accordance with another exemplary embodiment, a medical device may include an MRI guidewire and a connector as described above.

BRIEF DESCRIPTION OF THE DRAWINGS

FIG. 9 shows the embodiment in FIG. 8 with the contacts opened to allow the guidewire to slide in.

DETAILED DESCRIPTION

Lardo et al in U.S. patent application Ser. No. 09/536,090 "Magnetic resonance imaging guidewire probe," filed Mar. 24, 2000 (hereafter "Lardo '090"), the entire disclosure of which is herein incorporated by reference, disclose, among other things, a guidewire and associated devices for use with or as an MRI antenna. The connectors described herein may be used with any sort of guidewire or coaxial cable, not necessarily only those guidewire embodiments disclosed herein. Similarly, the guidewires disclosed herein may be used with any sort of connector, not only those embodiments disclosed herein.

Guidewires described herein may be inserted into lumens of various anatomic structures of a subject. In an embodiment, the guidewire is sized for insertion into a blood vessel. In an embodiment, the guidewire is sized for insertion into a human subject.

In MRI an external antenna (external with respect to the scanner, such as one being used as part of a guidewire) can receive electronic information from the MRI scanner. This information can be, e.g., control signals such as triggering information or transmit-receive gating signals. The antenna can provide RF signals containing, e.g., image information to be processed by the MRI scanner. The antenna can receive MRI signals generated from surrounding structures.

It would enhance the art to provide a low loss and reliable electrical connection between the antenna and the MRI scanner. It would further enhance the art to provide connectors that can be used in conjunction with guidewires, guidewire antennae, imaging needles and other antennas without diminishing the customary utility of these devices. It would also enhance the art to provide a connector that is easily removed and reattached to any contemplated guidewire, antenna, or the like.

Many MRI scanners currently known to the art are built to accommodate an external imaging antenna such as the guidewire antenna and may provide an external antenna port on the MRI scanner for that purpose. The external antenna port on an MRI scanner is often a single or multi coaxial or non-coaxial single and multi-pin connector, including BNC connectors, D-shell connectors, Lemo connectors, MMCX connectors, etc and other connectors known in the art.

Figure 1:
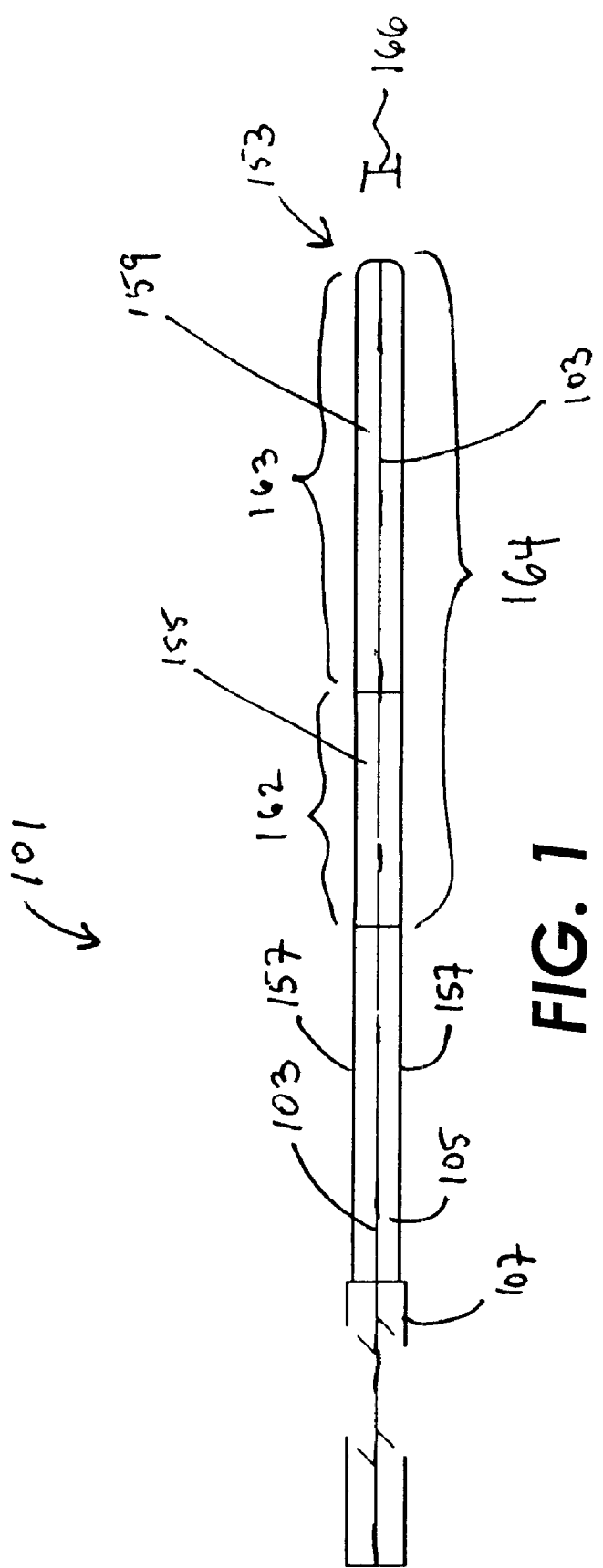
FIG. 1 shows one embodiment of the proximal end of a guidewire.

FIG. 1 shows a guidewire (101) that may be designed, in part, as a coaxial cable. Here the inner conductor (103) may be placed inside an outer conductor (157) and may be electrically separated from the outer conductor (157) by insulation (105). An additional layer of electrically insulating material (107) may be applied over the outer conductor to prevent electrical contact of the conductor to the user or patient. The outer diameter of such a guidewire may be, in one embodiment, less than about 0.040 inches, and preferably between approximately 0.012–0.038 inches. The inner conductor may have a diameter of around 0.004–0.012 inches. Materials are preferably nonferrous and nonmagnetic. This may help to prevent, e.g., image artifacts due to local magnetic field distortion, or motion of the guidewire caused by unwanted forces exerted by the magnetic field of the MRI scanner on the wire which could otherwise result in uncontrolled motion of the wire and cause harm to the patient. In an embodiment, the guidewire has a stiffness sufficient for insertion into a lumen of an anatomic structure of a subject. In an embodiment, the guidewire is sterilizable.

The distal end of the guidewire can terminate in an antenna, which could be any type of MRI antenna known to the art including looped, loopless, linear whip, or helical coil designs. An MRI antenna could be positioned anywhere along the guidewire. The guidewire may also include configurations of the distal end, such as a ribbon of a malleable substance, springs, and contoured wire shapes to improve steering of the guidewire and provide appropriate stiffness characteristics.

The guidewire can comprise a superelastic material such as the Tinol® range of materials (also known as Nitinol or NiTi). Some superelastics comprise titanium or a titanium-nickel alloy. Superelastics may be significantly deformed and still return to their original shape. These characteristics are advantageous in a guidewire due to the capacity to be severely deformed without damage and the resistance to kinking. Superelastic materials are also known for high biocompatibility and favorable mechanical characteristics within biological organisms or matter. Other biocompatible materials include, e.g., Silicone, PET, PE, Pebax, teflon, nylon, hytrel, latex, urethrane, titanium, and stainless steel.

In an embodiment, the guidewire is formed of MR-compatible materials. Examples of MR-compatible materials include but are not limited to MR-compatible stainless steel, brass, copper, bronze, Nitinol, other metallic materials that are non-magnetic, non-metallic substances such as carbon, glass fiber, or polymer, that can be plated with a layer of a good RF conductor such as copper, silver, gold, or aluminum either singly or in multiple layers, or any of the previous in any combination.

In a medical procedure, the distal end of the guidewire will be inserted into a patient, and using imaging techniques (such as MRI, X-Ray or other techniques), the guidewire will be maneuvered into a desired position, for instance near an arterial plaque. A medical device may then be threaded over the guidewire and also placed into position Often guidewires are positioned within a catheter or some other medical device, placed in a patient together, with the catheter lending support to the guidewire. This could be accomplished with a guidewire having a fixed or removable electrical connector at its proximal end by loading the guidewire into the proximal end of the catheter. A fixed connector, however, may prevent the removal or exchange of the catheter if the connector diameter is larger than the catheter's lumen diameter. In such a case, the guidewire would first be removed from the patient, the medical device exchanged, and the wire correctly placed again in the patient.

In contrast, a removable connector would permit device exchange without removing the guidewire from the patient. The connector could be removed from the guidewire, the guidewire extended with an extension wire affixed to at least a portion of the proximal end of the guidewire, the original device withdrawn, a new device inserted over the guidewire, the extension removed, and the connector reattached to the guidewire. If the medical device were a rapid exchange model, the guidewire might not need to be extended, but the connector would preferably be removed to pass the medical device over the entire length of the guidewire.

In an embodiment, the connector is formed of MR-compatible materials. Examples of MR-compatible materials include but are not limited to MR-compatible stainless steel, brass, copper, bronze, Nitinol, other metallic materials that are non-magnetic, non-metallic substances such as carbon, glass fiber, or polymer, that can be plated with a layer of a good RF conductor such as copper, silver, gold, or aluminum either singly or in multiple layers, or any of the previous in any combination.

In an embodiment, the connector may be repeatedly removed and reattached to the guidewire. This may be done, e.g., in the course of a medical procedure during which a plurality of medical devices are loaded onto and removed from the guidewire.

Such medical devices include, but are not limited to, balloon catheters for dilatation angioplasties, for stent placements, for drug infusions, and catheters for local vessel therapies such as gene therapies, radiation therapies; atherotomes and other devices for plaque resection and debulking; MRI imaging catheters; drug delivery catheters; intraluminal resecting tools; lasers and radio frequency and other ablative instruments. They could also include ultrasound imaging devices or optical coherent tomographic imaging devices. The devices would include but not be limited to those which perform a diagnostic or therapeutic role in the assessment or treatment of intravascular or intracavitary disease management.

As would be understood by one of skill in the art, in order for a guidewire to be most useful, it is preferable that a medical device be able to fit over the guidewire and for the device to be capable of placement over the guidewire after the guidewire is in position.

In order to connect the guidewire to the MRI machine's electrical signals so as to make it useful as an antenna, however, it is preferable to enable the very small guidewire to connect to the external antenna port on the MRI scanner, typically through a BNC connector, a multi-pin connector, or other connector. In one embodiment, the connector could be permanently attached to the proximal end of the guidewire. In another embodiment, the connector may be removably attached to the proximal end of the guidewire. In another embodiment, the connector may be dimensionally adapted to allow the catheter or other medical device to be placed over both the connector and the guidewire. In another embodiment, the proximal end of the guidewire may be dimensionally adapted to have relatively the same diameter as the rest of the guidewire.

The proximal end of the guidewire can be specially designed to provide surfaces for connecting to both inner and outer coaxial conductors while maintaining mechanical strength and not risking breakage or bad connection from having to thread the narrow inner conductor directly into some type of fitting capable of making an electrical connection.

Similarly, the proximal end can be adapted to fit an extension wire to permit device exchange capability as well as the electrical connection.

FIG. 1 shows the proximal end of a guidewire utilizing one embodiment to make connection to the inner conductor in some embodiments simpler and more reliable. In FIG. 1, the inner conductor (103) and the outer conductor (157) extend beyond the end of the outer insulation (107) to expose conductive areas for electrical contact. The inner conductor (103) extends further, beyond the proximal end of the outer conductor (157), thereby exposing an extended section (164) on which to make contact to the inner conductor (103). The extended section has an insulated area (162) and an inner conductor contact (163). The inner conductor contact (163) includes an electrically conductive material (159) that may be built up around the inner conductor (103). This facilitates the easy insertion of the proximal end (153) of the guidewire (101) into the connector, and helps to maintain maximum strength in the extended section (164). In an embodiment, the inner conductor (103) may be built up with electrically conductive material, preferably nonmagnetic (such as brass tubing) to approximately the same diameter (166) as the outer conductor (157). The inner conductor contact (163) may be radially disposed about a portion of the extended section (164). In an embodiment, the inner conductor contact (163) is built up to a smaller diameter than that of the outer conductor (157). In an embodiment, the inner conductor contact (163) is built up to a larger diameter than that of the outer conductor (157).

Figure 6:
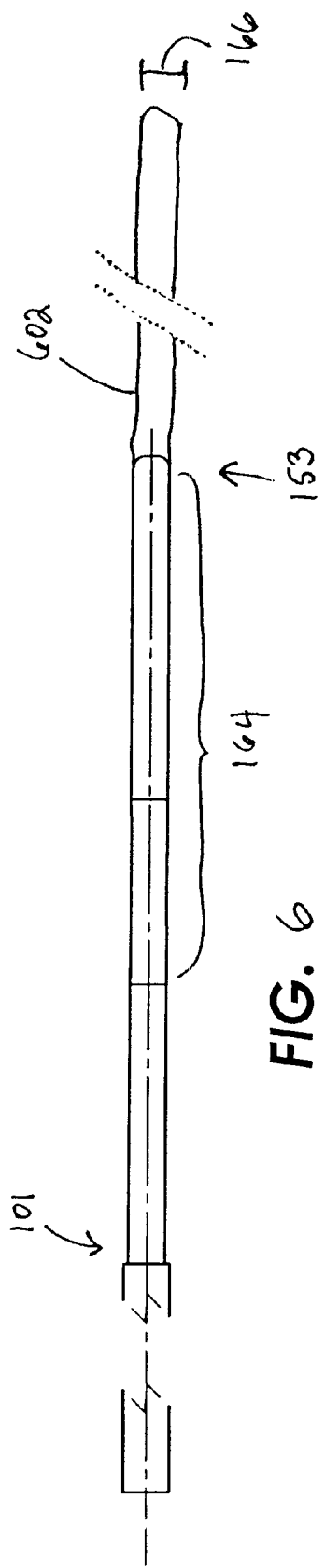
FIG. 6 shows an embodiment of a guidewire with an extension attachment.

As shown in FIG. 6, at least a portion of the extended section (164) may be configured to accept an extension attachment (602). In an embodiment, the attachment (602) has a diameter substantially equal to diameter (166) as the guidewire (101). The extension attachment can add a length to the proximal end (153) of the guidewire (101) that may be long enough to permit medical device exchanges without displacing the guidewire (101) from its position in-situ. The attachment mechanism may include, but is not limited to: matching threads on the attachment and extended section (164) for screwable attachment; a tube to tube slip fit or snap fit; or a coiled spring fitting into a appropriately sized tube. Any of these configurations could be interchangeably incorporated on any portion of extended section (164) area of the guidewire (101), or the extension attachment. Other attachment mechanisms known in the art may also be employed. In an embodiment, the extension attachment is attached to the inner conductor.

Referring again to FIG. 1, the insulated area (162) can be built up with an electrically insulating material (155) to prevent potential short circuiting between the outer conductor (157) and the inner conductor (103) or inner conductor contact (163). The built-up insulating material (155) can also provide rigidity for the proximal end (153).

This configuration converts the two concentric coaxially oriented conductors to a pair of contacts that are exposed to the connector in a sequential axial configuration, both of which are relatively the same diameter as the outer conductor. In one embodiment, the coaxial relationship can then be maintained by the design of the connector from that point to an interface circuit, or the MRI scanner, while still allowing for easier connection to the connector.

The interface circuit may include capacitors, inductors, resistors, diodes, and other electrical and electronic elements to couple the signals from the guidewire (101) ultimately to an MRI scanner. The interface circuit may be coupled to each of the contacts in the connector. The interface circuit may include a tuning/matching circuit. The interface circuit may include a decoupling circuit. The interface circuit may include a balun trap. The interface circuit may also provide high voltage protection for the guidewire and any subject into which the guidewire may be inserted during use. DC in excess of a predetermined threshold may be isolated from the electrical signal applied to the guidewire via DC blocking/RF bypass capacitors. The interface circuit may also include a connection detector to signal the user or scanner in the event of disconnection between the guidewire and connector. The interface circuit may also include an identification system to identify the coil to the connector or to the scanner with a coding scheme.

The connector adapted for coupling to the inner conductor contact (163) can be of many types; exemplary embodiments are provided below. One of skill in the art would recognize additional connector types and those types are also included in this disclosure.

Figure 2:
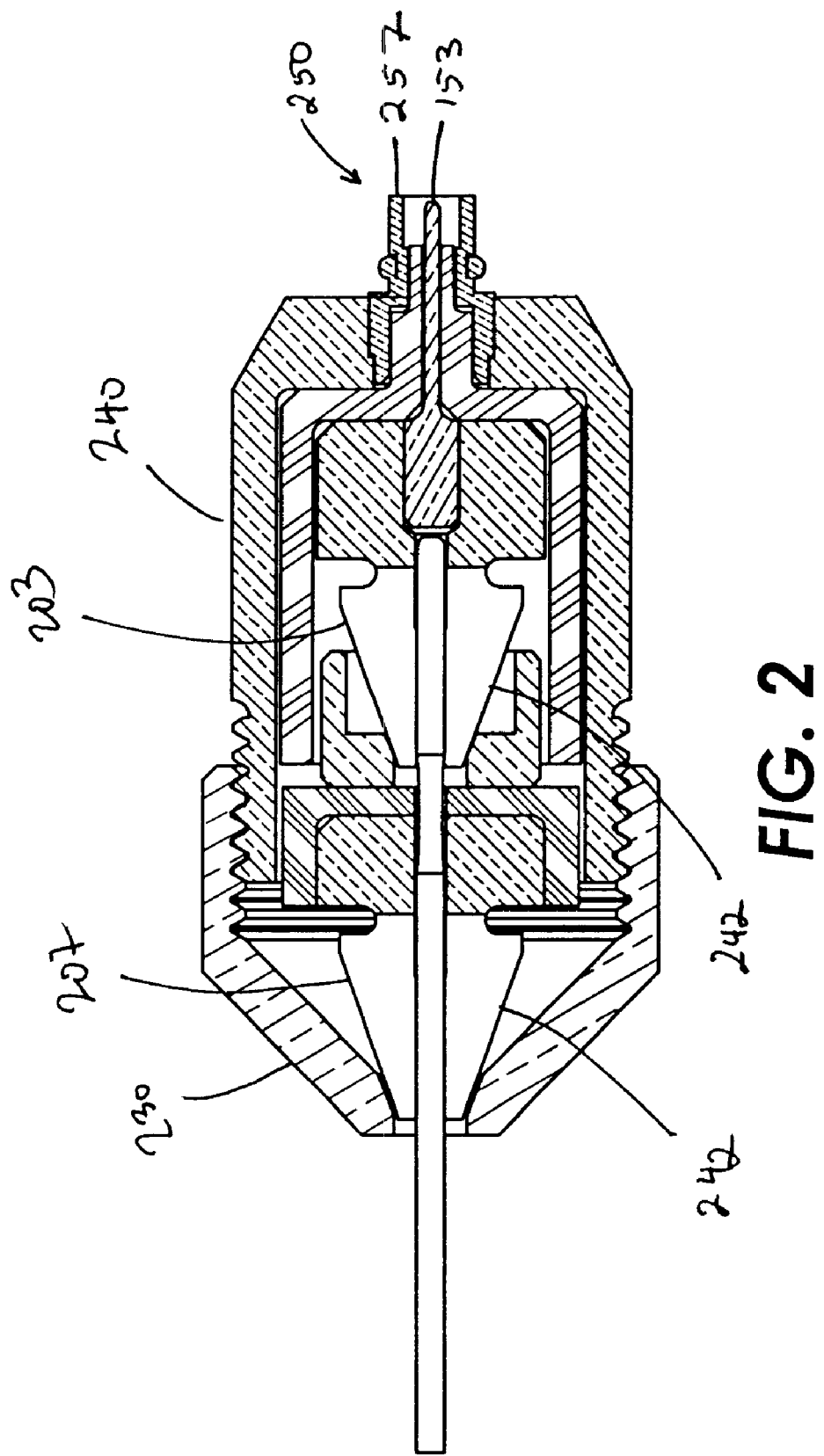
FIG. 2 shows one embodiment of a collet style clamping connector.
Figure 3:
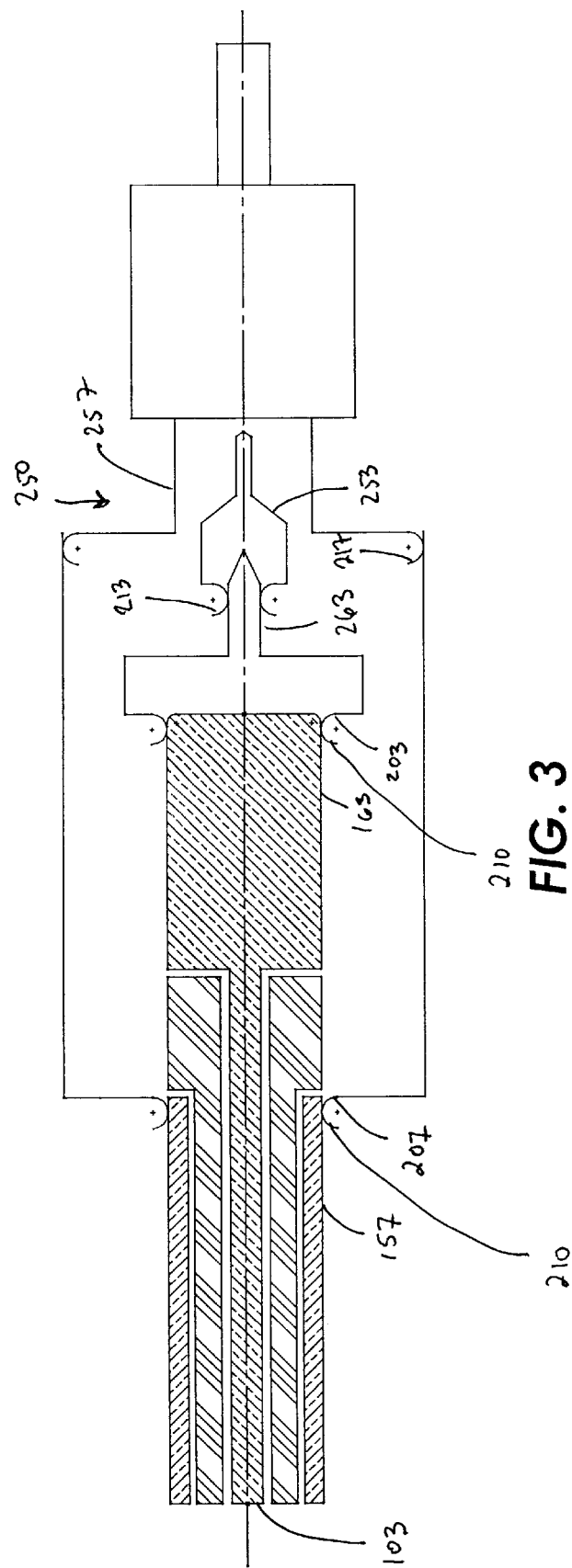
FIG. 3 shows one embodiment of the internal connection detail of a collet style connector such as that shown in FIG. 2.

In an embodiment, two conductive collets are positioned in line coaxially with the guidewire, as shown in FIG. 3. A first collet (203) makes contact with the inner conductor contact (163) of the inner conductor (103). A second collet (207) makes contact with the outer conductor (157). These two collets remain electrically isolated from each other. Isolation may be maintained by, e.g., physical separation or by imposition of an insulating material between them. The collets may come into contact with the appropriate conductors through any method or system known to the art. One method is to compress the collets axially to provide a clamping force on the guidewire contact surfaces via the angled outer surface (210) of the collets. This can be achieved using a cap with threads or with cams to produce axial motion when rotated relative to the body of the connector. One embodiment of such a cap (230) and tapered collets (203, 207) is shown in FIG. 2. In an embodiment, the collets are flexible and resilient.

When connecting the guidewire to the connector, the connection between the outer conductor contact (157) and the distal collet (207) contact can be easily confirmed manually by lightly tugging or twisting the guidewire relative to the connector. Mechanical clamping may be desirable in one embodiment because it can, e.g., facilitate steering the guidewire. A physician or other operator of the guidewire can use the connector as a handle. Mechanical clamping can also prevent inadvertent removal of the guidewire from the connector. The increased diameter (and potential gripability through texturing of the body (240)) of the connector can enable the operator to achieve greater torque control on the guidewire as a whole and at the distal tip where steering is performed. The increased torque control can improve the ability of the operator to steer the guidewire through twisting pathways.

In an embodiment, the inner and outer conductor contacts can form annular shapes. In an embodiment, the insulated area may form an annular shape. In an embodiment, any of the inner conductor contact, the outer conductor contact, and the insulated area may form a "C" shape. In an embodiment, any of the inner conductor contact, the outer conductor contact, and the insulated area may form a series of interrupted patches around the circumference of the guidewire.

In an embodiment, the proximal contact may couple to the outer conductor contact, and the distal contact may couple to the inner conductor contact.

To ensure a good mechanical and electrical contact is made on the enclosed inner conductor, the clamping angle of the proximal collet (203) can be reduced so that it will clamp the inner conductor contact before the distal collet (203) will clamp the outer conductor under axial movement. Therefore when the outer conductor contact is confirmed manually, the inner contact is also ensured.

In operation, the cap of FIG. 2 would slowly compress the collets (203) and (207) as the cap (230) may be screwably displaced along the connector body (240) by pushing relatively solid components of the cap or body into the angled sides (242) of the collets. One of skill in the art would recognize that many other attachment methods other than screwably connecting could be used and all such other methods are included within the scope of this disclosure. Some alternatives to the threads or cams for axial locking motion include, but are not limited to, a lever that may be integrated into the connector body to produce this action or an axially sliding sleeve with a return spring and/or detents.

In order to maintain the coaxial nature of the conductors, such as for providing shielding, the signal path for the outer conductor (157) may be from the distal collet (207) to the cap (230) and body (240) of the connector, and to the outer sleeve (257) of the rotating contact (250). This rotating contact can be any type of coaxial (or other if the coaxial nature is not desired to be maintained) connector such as a standard BNC connector, or a standard MMCX connector, or any other standard or nonstandard connectors known in the art now or in the future. In one embodiment, this contact (250) can then be connected by any method known in the art, to the antenna output of the MRI scanner including, but not limited to, the use of a cable, or by methods of wireless transmission.

The signal path for the inner conductor (103) may be from the proximal collet (203) to a center pin (263) which can be connected directly to, or be made from the same contiguous part as, the inner pin (253) of the contact (250). In an embodiment, the proximal collet (203) and center pin (263) are disposed inside the outer signal path to maintain coaxiality throughout the connector. In an embodiment, one or both of the proximal collet (203) and center pin (263) are not disposed inside the outer signal path. In an embodiment, the contacting components may be plated with an oxidation resistant material such as gold to enhance connection quality. Further, in one embodiment, additional rotating contacts (213) and (217) as shown, e.g., in FIG. 3, may be provided to enable rotation of the connector relative to any cables or devices connected to the output terminal. This rotational capability of the connector can also be accomplished through coaxial contacts with a smooth sliding fit to the stationary socket.

Figure 5:
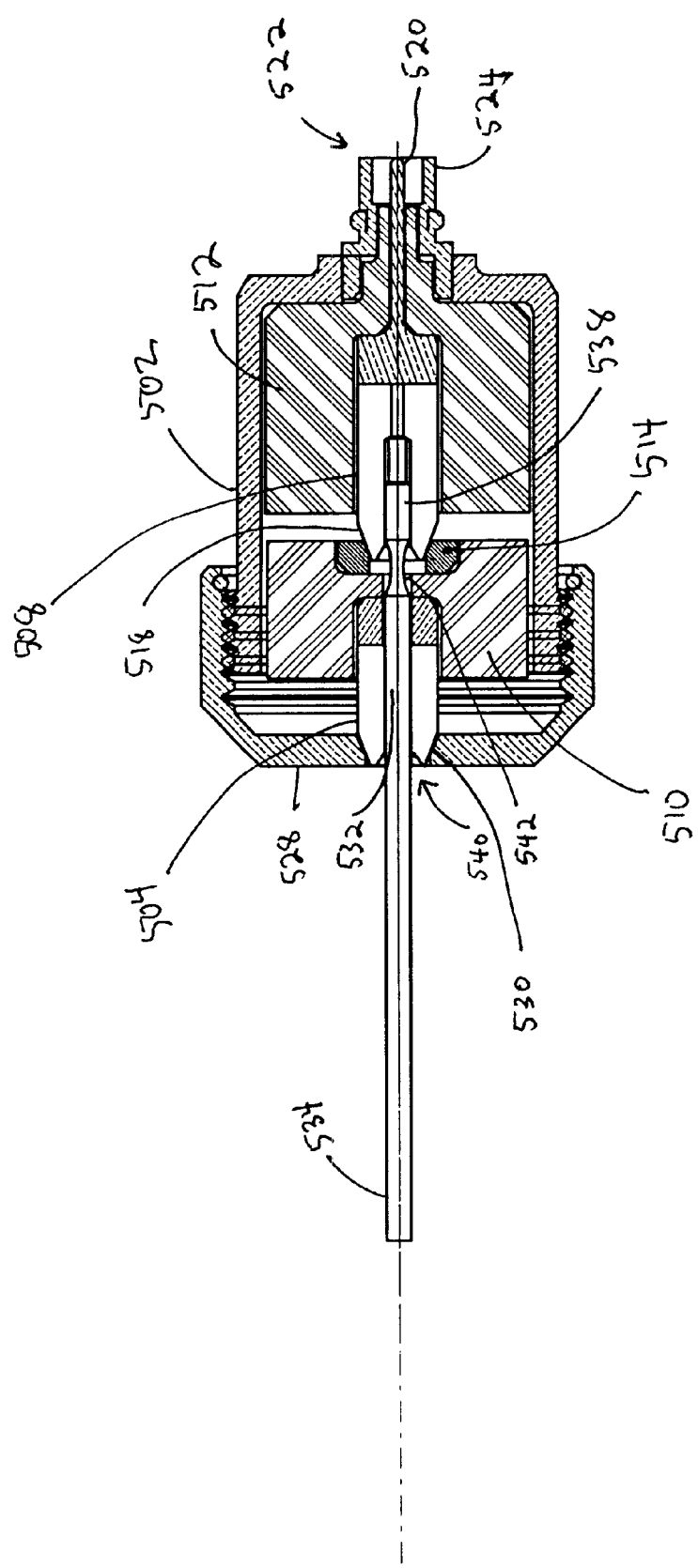
FIG. 5 shows another embodiment of a collet style clamping connector.

FIG. 5 shows another embodiment of a collet style clamping connector. The body (502) may contain a distal collet clamp (504) and a proximal collet clamp (508) arranged longitudinally. A distal insulator (510) may surround the distal collet clamp (504) and insulate it from the body (502) and/or from the proximal collet clamp (508). The distal insulator (510) may also center the distal collet clamp (504) in the body (502). The distal insulator (510) may include a material having a dielectric constant. A proximal insulator (512) can similarly surround the proximal collet clamp (508) and may include a material having a dielectric constant. The proximal insulator (512) may insulate the proximal collet clamp (508) from the body (502) and/or from the distal collet clamp (504). A proximal clamp ring (514) may be positioned between the distal collet clamp (504) and the proximal collet clamp (508), contacting the distal insulator (510) and engaging the angled surface (518) of the proximal collet clamp (508). The distal insulator (510) may insulate the distal collet clamp (504) from the proximal clamp ring (514). The distal and proximal clamps (504, 508) may also be insulated from each other by physical isolation from one another. On the end opposite the angled surface (518), the proximal collet clamp (508) can terminate in a center pin (520) of a plug (522).

The plug (522) may be an output terminal including a single or multi coaxial pin or non-coaxial single and multi-pin connector, including BNC connectors, D-shell connectors, Lemo connectors, MMCX connectors, etc and other connectors known in the art. In an embodiment, the proximal contact (508) may extend axially to the plug (522) to form the center pin (520). The center pin (520) may be surrounded by an outer adapter (524). The plug (522) can have a mechanism for secure but rotatable and removable attachment to a mated connector (not shown). The mechanism may include, e.g., a spring-loaded cuff (528) that fits into a corresponding retaining ring or groove of the mated connector. A cap (528) may screwably attach to the body (502).

A guidewire (534) may be inserted into the connector through an orifice (540) and into a channel (542). The channel (542) may define an insertion path for an end of the guidewire (534) in to the connector. The cap (528) may then be screwed onto the body (502), to secure the guidewire (534) in the connector and to form electrical contacts. The cap (528) can engage an angled surface (530) of the distal collet clamp (504). This may cause the distal collet clamp (504) to touch an outer conductor contact (532) of the guidewire (534). Compression of the cap (528) against the distal collet clamp (504) may also cause the distal collet clamp (504) to push against the proximal clamp ring (514), which in turn can engage the angled surface (518) of the proximal collet clamp (508), causing it to touch a inner conductor contact (538) of the guidewire (534).

An electrical signal from the inner conductor contact (538) of the guidewire (534) can follow an inner conductor path that may include the proximal collet clamp (508) and the center pin (520) of the plug (522). In an embodiment, the inner conductor contact (not shown) of the guidewire (534) extends axially to the plug (522) to form the center pin (520). An electrical signal from the outer conductor contact (532) of the guidewire (534) can follow an outer conductor path that may include the cap (528), the body (502), and the outer adapter (524) of the plug (522).

Any of the contacts described herein may have an annular shape; may extend around the full circumference of the channel; may extend around a portion of the circumference of the channel; may extend around multiple portions of the circumference of the channel; or may extend around the full circumference of the channel with interruptions.

The impedance of the connector can be matched to that of any MRI scanner by adjusting the relative dimensions of the inner and outer conductor paths and the dielectric constants of the insulators (510, 512). The materials of the insulators (510, 512) may be any electrically insulating substance or air. In an embodiment, the insulators (510, 512) include a fluoropolymer. The insulators (510, 512) may include polyethylene, a foamed material incorporating air in the structure, ceramic, or other materials with appropriate dielectric and mechanical properties.

The guidewire (534) may be secured in the connector by other securing mechanisms. In an embodiment, the connector includes a gripper that contacts the guidewire (534) and holds in relative longitudinal position with respect to the guidewire. The gripper may be actuated by, e.g., a lever, collet, snap, button, dial, cam, or other device known to one of skill in the art.

In an embodiment, the connector may be provided with a sliding contact. This may take the form of, e.g., a spring piston on the inside of the channel (542) through which the guidewire (534) inserts. The piston can push against the guidewire (534), releasably making electrical contact.

In an embodiment, the connector may be provided with a coil wound against the inner wall of the channel (542). The coil may be dimensionally adapted to releasably grip the guidewire (534) as it is inserted into the channel (542). The coil can be deformed, e.g., by bending, tilting, or pressing out of round, to allow enough radial deflection to prevent binding of the guidewire (534) during, e.g., insertion or removal.

In an embodiment, the channel (542) may be provided with slots, dimples, or dents. These permit the channel (542) to expand slightly during insertion of the guidewire (534) and to grip the guidewire (534).

In an embodiment, a tubular mesh of wire may be deployed within the channel (542). As the guidewire (534) is inserted, axial compressive force may be exerted on the mesh by the guidewire, causing its diameter to increase slightly and permit further insertion of the guidewire (534). Once the guidewire (534) is inserted, the mesh can remain in contact with it.

In an embodiment, the guidewire (534) may be rotationally fixed with respect to the connector. This facilitates rotation of the guidewire by gripping and rotating the connector. Such a manipulation may be desirable, e.g., to rotate a portion of the guidewire (534) that is inside a subject. The connector may be rotationally free with respect to the mated connector. This prevents the creation of torsion in the guidewire (534) or at the point of connection of the plug (522) to the mated connector.

In an embodiment, the guidewire could be secured and rotationally fixed with respect to the connector by screwably attaching the guidewire to the connector. Threads could be provided on, e.g., the outer contact and/or inner contact of the guidewire, with corresponding threads on the distal and/or proximal contact of the connector.

Figure 8:
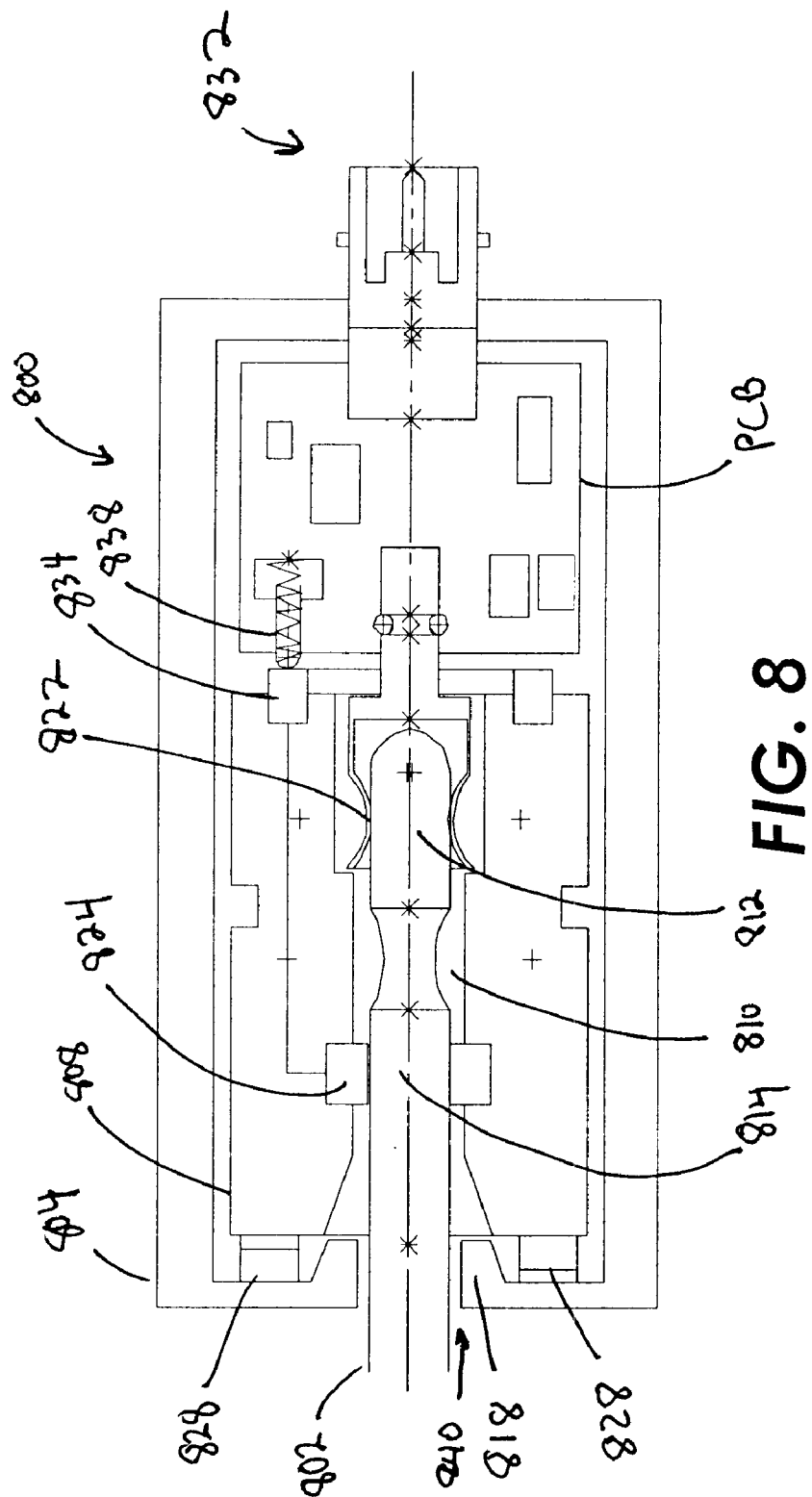
FIG. 8 shows an embodiment of a clamping connector that permits rotation of a guidewire relative to the connector.

FIG. 8 shows an embodiment in which the guidewire (802) may be rotationally free with respect to the connector (800). In another embodiment the connector body (804) provides RF shielding by using an electrically conductive material or by applying a conductive layer to a non-conductive body material.

The connector (800) may include a contact carrier (808). The contact carrier (808) may be made of a non-conducting material. It can hold one or more contacts (822, 824) exposed to a channel (810) to connect to the guidewire contacts (812, 814) electrically, and mechanically connect to at least one surface of the guidewire (802) with sufficient force to retain the guidewire (802) while being pulled axially. The contact carrier (808) may surround the channel (810). When the carrier (808) is in its closed (free) state, the contacts (822, 824) exposed to the channel (810) are in contact with the guidewire contacts (812, 814).

Figure 9:
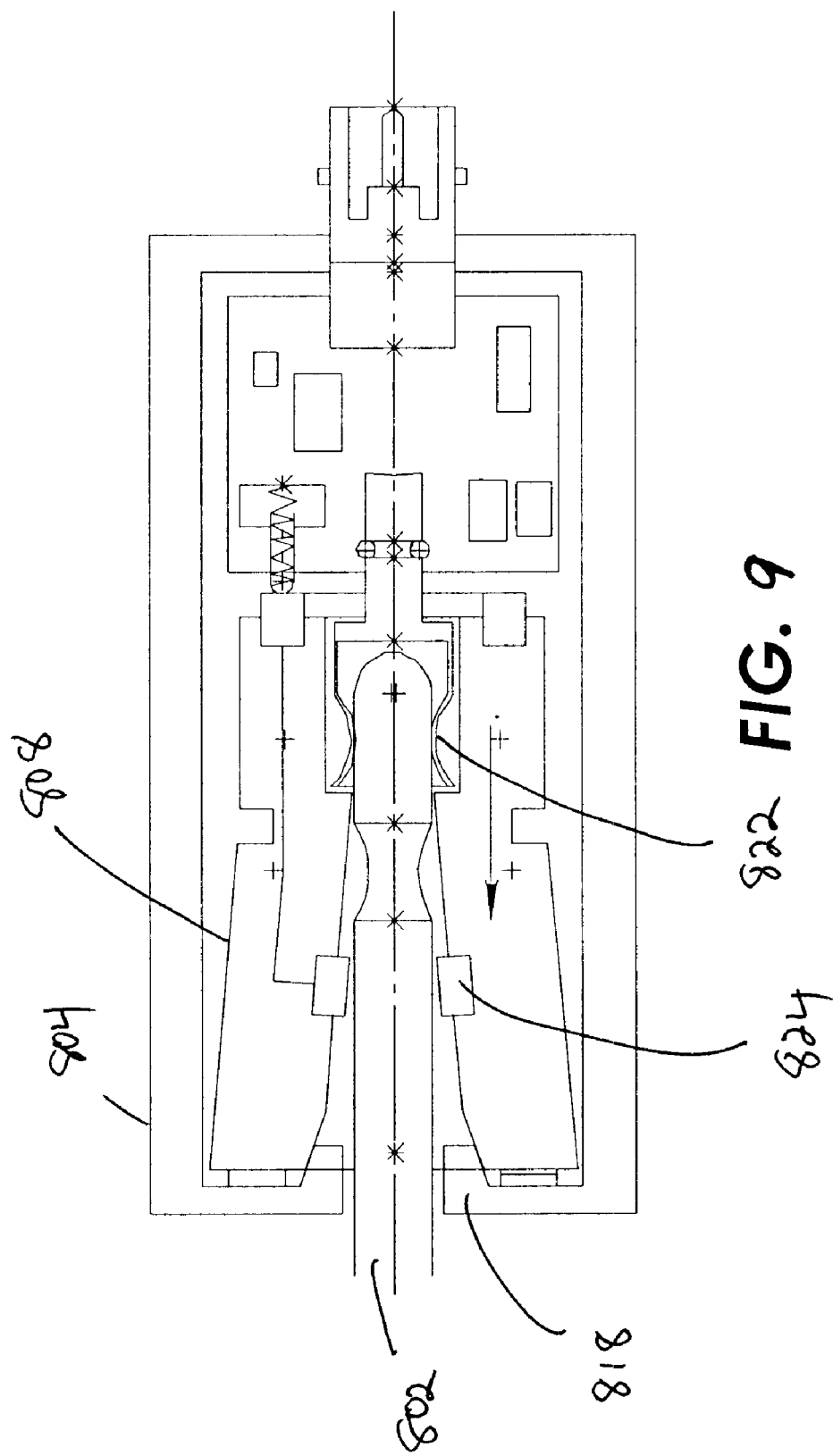

The carrier (808) can be spring loaded (as by, e.g., springs 828) or include an elastically bendable material allowing it to be deformed by pushing it against a conical wedge (818) at the front of the body (804) and disposed between the carrier (808) and an orifice (840). The springs (828) may be disposed between the wedge (818) and the carrier (808). The carrier (808) may optionally be made pliable by providing, e.g., slots (1002 in FIG. 10) or other interruptions in the carrier (808). This deformation can open the carrier (808) radially, moving at least one of the contacts (822, 824) outward, as shown in FIG. 9. This opening provides clearance for the guidewire (802) to be inserted with less interference than for the carrier (808) in the closed (free) position. When released, the carrier (808) will return to its free position by sliding proximally and off of the wedge (818), allowing the contacts (822, 824) to clamp the guidewire (802) and allowing the carrier (808) to rotate relative to the body (804). In an embodiment, the contacts (822, 824) present no obstructions to the free rotation of the guidewire (802) within the channel (810).

Figure 10:
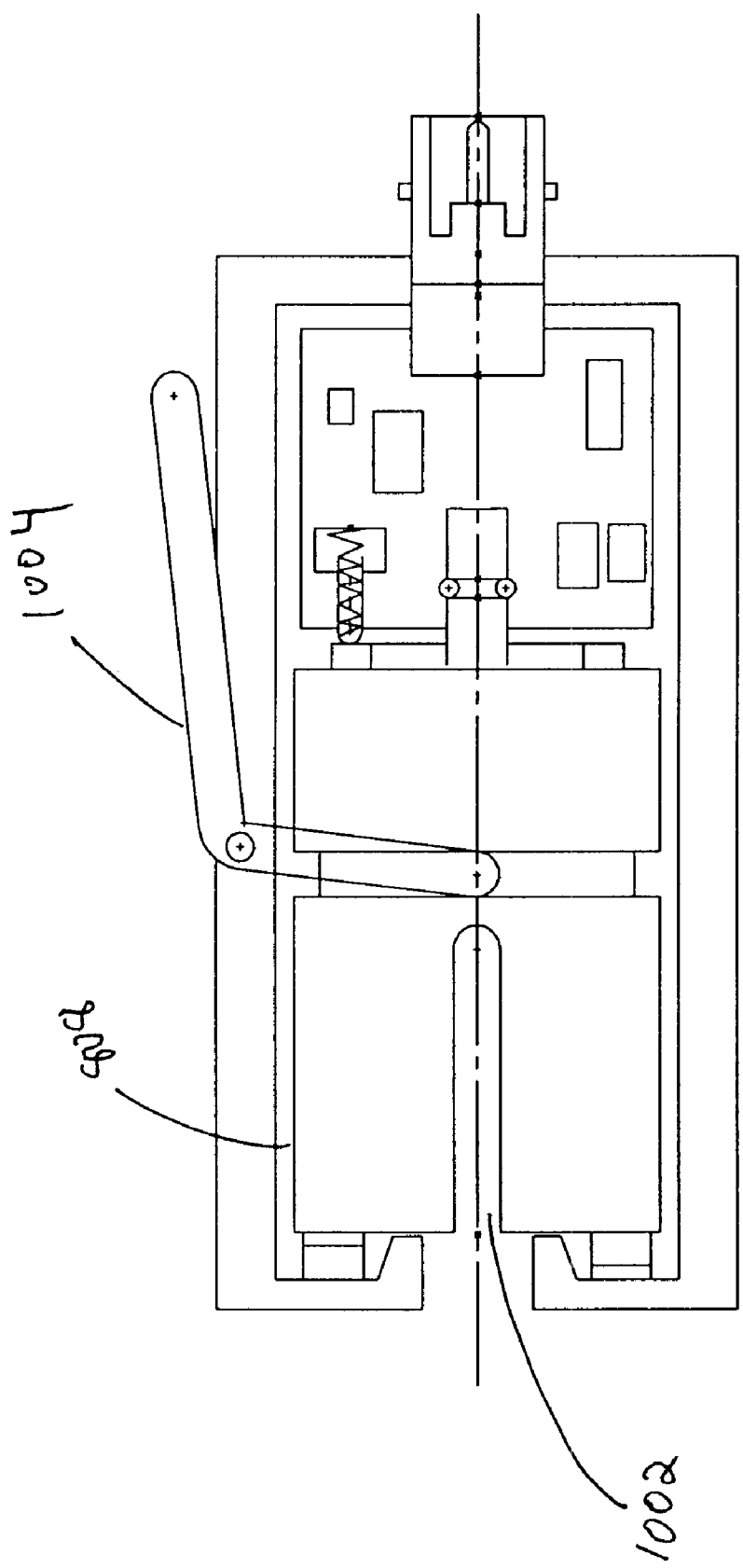
FIG. 10 shows a cutaway view of an embodiment of a clamping connector with a securing mechanism having a lever.

The carrier can be actuated (i.e., moved from the closed or free position to an open position) by a number of mechanisms, such as by a lever (1004) as shown in the cutaway view of FIG. 10. In an embodiment, the lever (1004) may be depressed, thereby moving the carrier (808) distally and causing it to open. A lever facing in the opposite direction and lifted to actuate the carrier (808) can also be used. Alternatively, the connector can be configured such that axial movement can be produced when one component can be rotated relative to another, as with a cam or threads. A slide or button could also be used.

In an embodiment, e.g., as shown in FIG. 8, the outer contact (824) can be provided as an active clamping contact that may be applied to and released from the guidewire (802) via actuation of the carrier (808). This provides electrical contact and good mechanical clamping on the outer contact (814) of the guidewire (802), which may be stronger than that of the inner conductor (812). This may make the outer contact (814) a preferred portion of the guidewire (802) for mechanically fixing the guidewire (802) to the carrier (808). The outer connecter contact (824) can have one or more conductive parts mounted in the carrier (808) and connected to a rotatable contact behind or outside the carrier. This can be done using a conductive ring (834) in slidable contact with a spring-loaded plunger (838) or with a stamped flat contact. These may be mounted on a printed circuit board (PCB) or directly to the outer adapter of, e.g., a BNC (832) or to the body (804). In another embodiment, the distal contact may be a passive slip type contact and the guidewire is mechanically fixed to the carrier in a location other than the distal contact.

The inner contact (822) can be, e.g., an active clamping, or a passive slip fit type of contact. As a passive contact, it could contact the proximal guidewire contact (812) using, e.g.: a wire oriented perpendicular to the channel and having a surface tangent to the channel; a patch, strip, or ring of formed or stamped metal placed adjacent to the channel; a coiled or deformed coil spring, providing a contact and gripping surface; a tube modified with slits or dimples to permit expansion and clamping; or with a tubular mesh that can expand or clamp with axial movement of the guidewire. A portion of a formed contact, e.g., the end exposed to the channel, may be oriented tangentially with respect to the channel. The inner contact (822) may include a springloaded piston which allows the wire to pass but maintains contact while in place.

An electrical signal received by any of these types of contacts may be coupled to, e.g., a ring (834), an outer adapter of a connector, or the connector body. In addition to the rotational movement this can allow axial movement via sliding or flexible contact to allow the carrier to be actuated. A coil spring may be deformed on it perimeter, i.e., by bending the turns of the coil out of round to conform to, e.g., a triangular or rectangular shape. Such perimeter deformation can provide an electrical contact and can provide gripping and removal resistance. A spring may also be longitudinally deformed, in which the spring is bent away from its straight-line shape, so that it can provide an electrical contact and can provide gripping and removal resistance.

The outer contact (824) may also have a wire, a patch or ring of formed or stamped metal, a spring, tube, or mesh, as described above.

Figure 11:
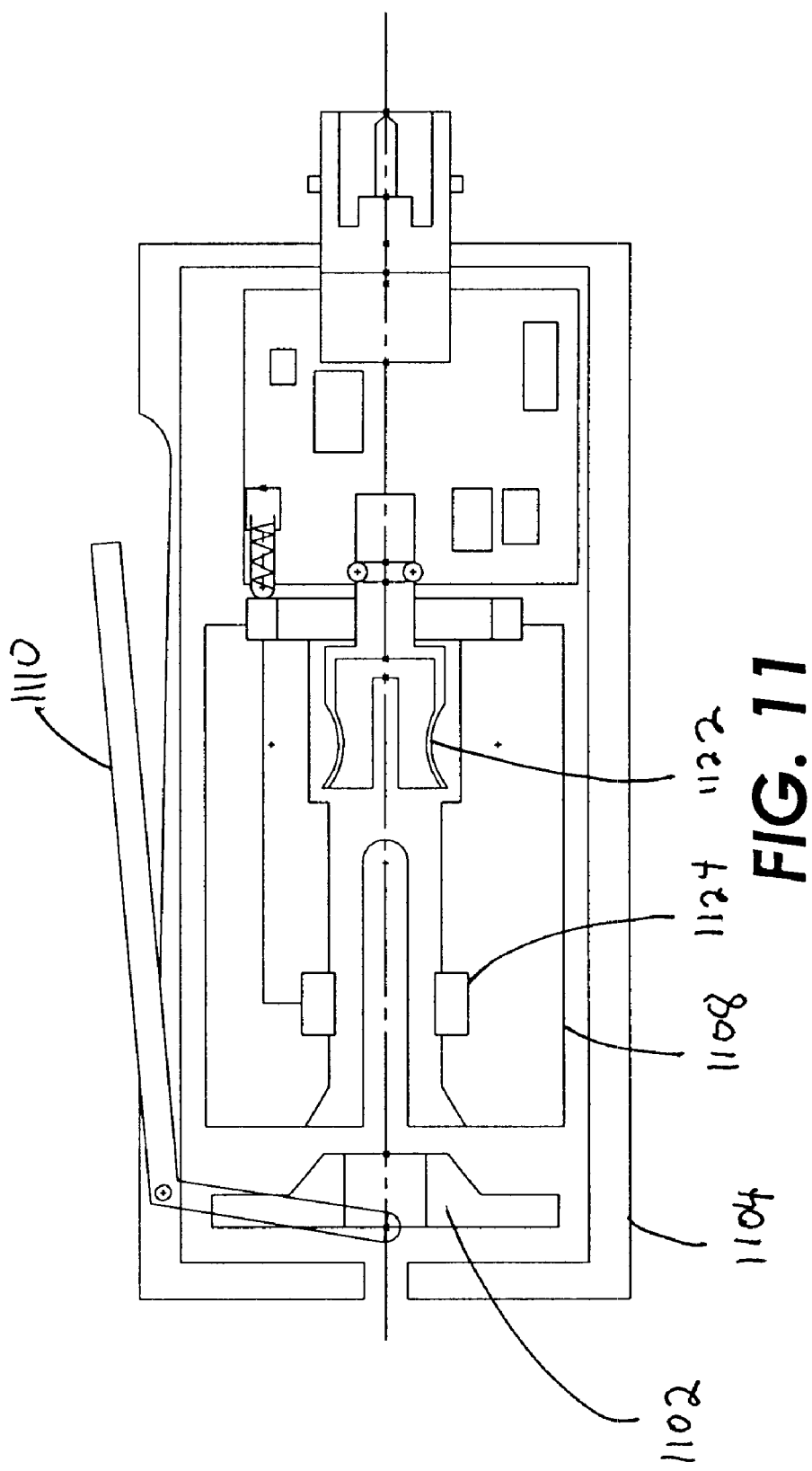
FIG. 11 shows another embodiment of a clamping connector with a securing mechanism having a lever.

FIG. 11 shows an embodiment wherein the wedge (1102) can be separate from the connector body (1104). This facilitates the actuation of the carrier (1108) to open the at least one of the proximal and distal contacts (1122, 1124) without the need for axial movement of the carrier (1108), thereby simplifying the electrical connections from the carrier (1108) to the body (1104) of the connector. Actuation can be accomplished, e.g., by lifting a lever (1110) away from the body (1104), causing the wedge (1102) to move into the carrier (1108). Other securing mechanisms described herein and known to the art may also be employed.

In an embodiment, additional contacts can be incorporated into the guidewire channel to provide any contacts needed for detecting the presence or absence of the guidewire contact.

Figure 4:
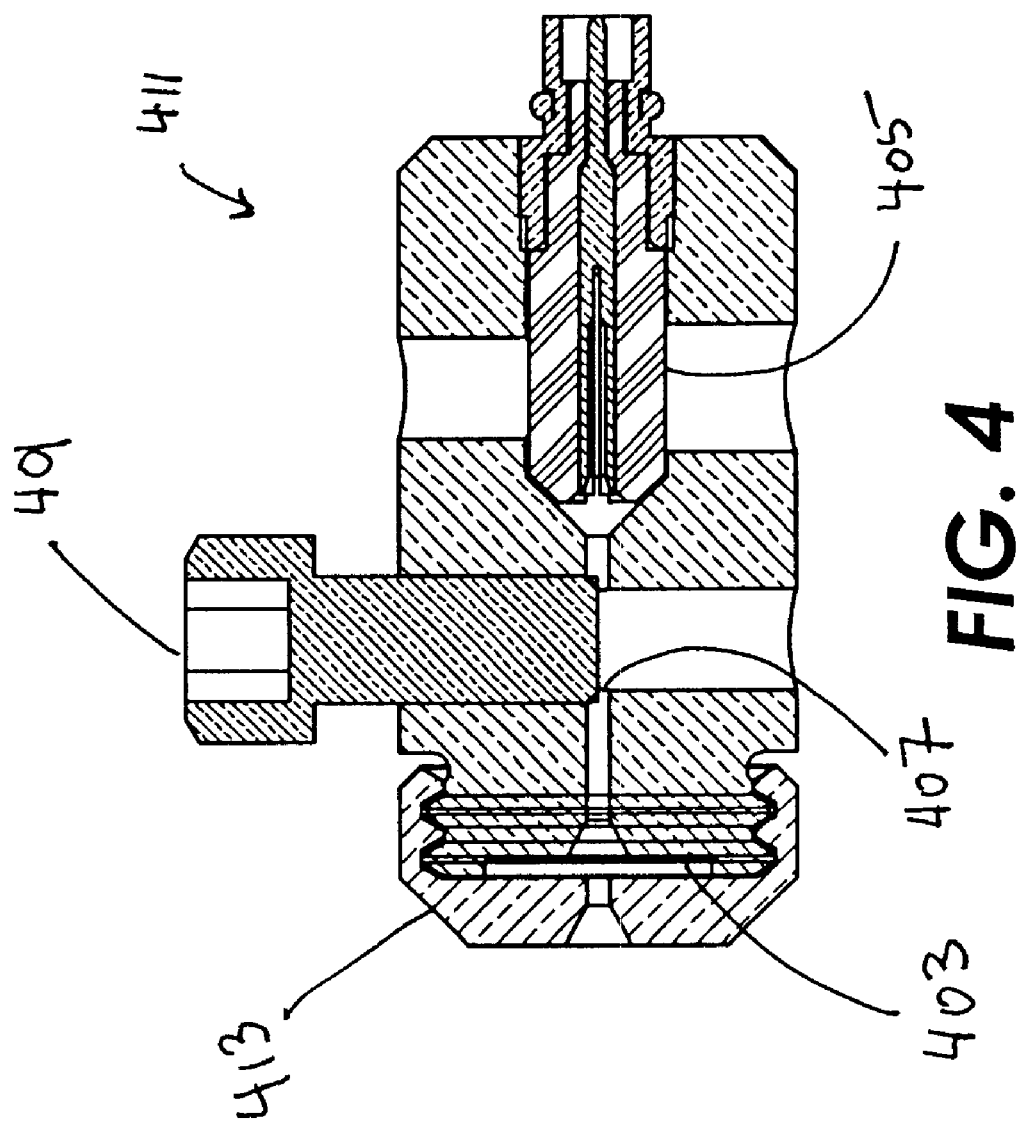
FIG. 4 shows one embodiment of a Radial/Tubular clamping connector.

In another embodiment depicted in FIG. 4, the connector (411) may include a pair of coaxial tubular contacts. The proximal contact section of the guidewire may be inserted into the connector to couple with the contacts. These contacts could include, e.g., a slip fit on the guidewire contacts, or an active radial clamping action that can be applied to positively hold the tubular contacts on the guidewire contacts. These could also be combined, such as a sliding contact (405) for the inner conductor/proximal connection and a radially clamping contact (407) for the outer conductor/distal connection.

An active clamping configuration has the advantage of a secure mechanical connection when electrically connected, allowing the connection to withstand some tensile and torsional loading while the guidewire is manipulated. Radial clamping action can be applied by, e.g., a screw, spring, plunger or lever (401), which can be levered to compress, bend, or apply friction to the guidewire when it is within the connector tubes. The tubes could be made from a conductive material with slots to allow flex for clamping, or alternatively from a metal spring or a flexible conductive material, such as a plastic with an electrically conductive coating or filler.

Because intravascular procedures commonly result in some blood or other bodily fluids on the operators' gloved hands, it may be desirable to position a wiper or seal at the entry of the connector, and such a wiper can be included on any type of connector in an embodiment. Saline solution and other fluids are also commonly present during these procedures. This wiper would minimize the introduction of fluids and other contamination into the connector by wiping the surface of the guidewire tip as it is inserted into the connector and block spilled fluids from entering the connector. The entry of such fluids into the connector could increase signal noise from degradation of the connection, or could cause a failure in the operation of the guidewire as an antenna. This wiper can be made from a soft flexible material such as silicone. It could have slits and/or a hole to allow passage of the guidewire into the connector or the guidewire could be contoured so as to punch a hole through the wiper upon insertion. One embodiment of a wiper (403) is depicted in FIG. 4. In an embodiment, the wiper (403) can be disposed within a wiper cap (413). In an embodiment, the wiper cap (413) screwably attaches to the remainder of the connector (411).

Connectors may be removable from the guidewire when desired by the operator. Further, a medical device can be threaded over a guidewire without having to overcome significant variations in diameter. Therefore the guidewire can be placed in position, the connector can be removed allowing a catheter to be threaded over the guidewire, and the connector can be reattached to enable additional imaging with the catheter in place.

In an embodiment, the housing for the connector also contains an interface circuit, such as one described in Lardo '090, for the MRI scanner. This would provide the benefit of a single component for the user to connect and coordinate during the procedure.

Figure 7:
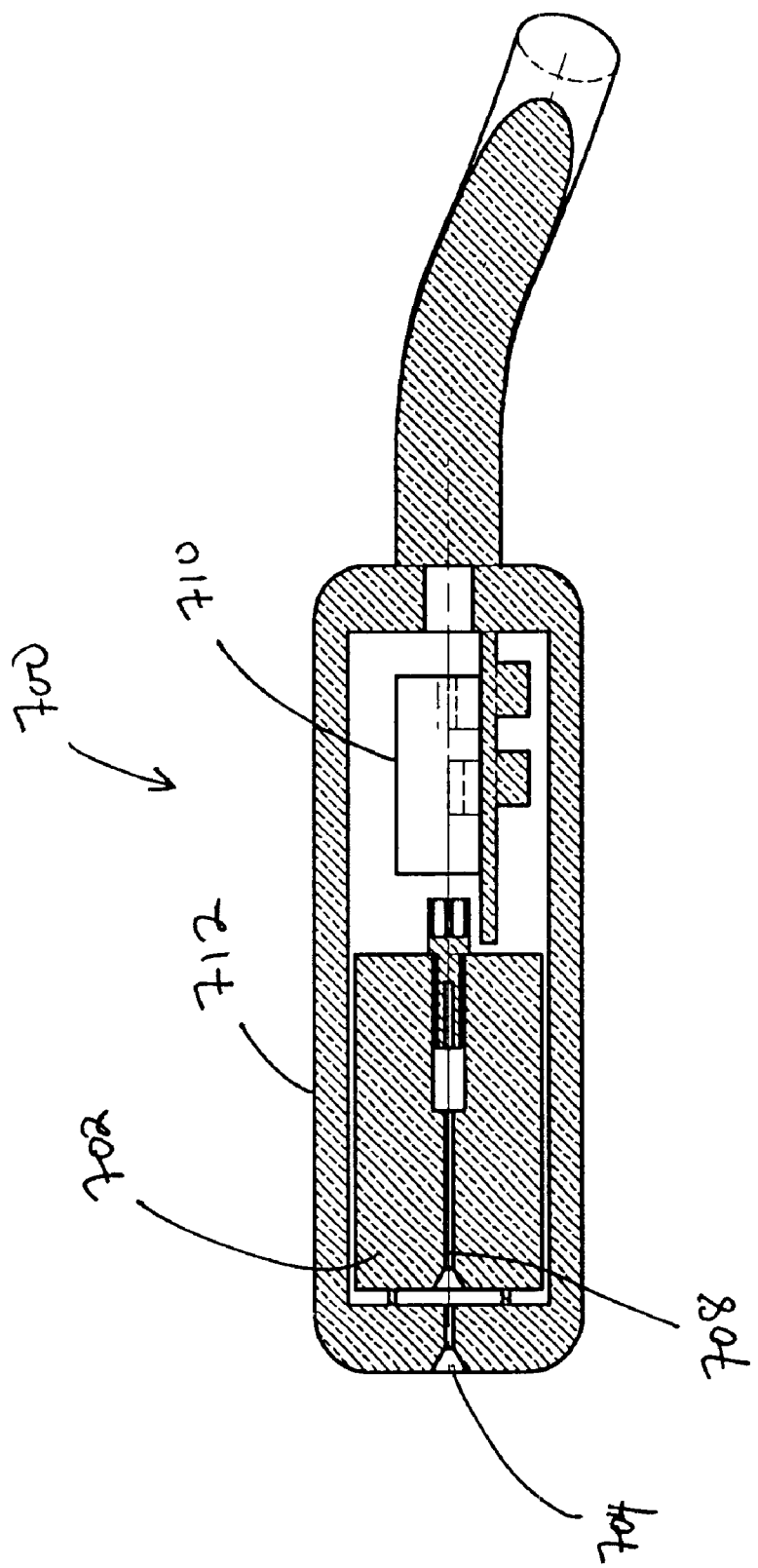
FIG. 7 shows one embodiment of a connector integrated with an interface circuit.

As depicted in FIG. 7, the interface circuit and the connector may be combined in a single housing as a combined connector (700). Such an arrangement eliminates one connection that links the guidewire to the MRI scanner. This can make the system more reliable, can lessen the risk of disconnection during operation, can reduce cost of the system, and can reduce the number of discrete parts that must be handled by operators of the MRI imaging apparatus.

A guidewire may be inserted through an orifice (704) into a channel (708) within the contact carrier (702). The guidewire may be secured in the contact carrier (702) by any of the securing mechanisms described herein or known to one of skill in the art.

In any of the embodiments described herein, the body of the connector can provide shielding to prevent RF interference by use of a conductive material for the body, or a conductive layer on a nonconductive material. All materials are preferably nonmagnetic to prevent interaction with the magnetic field of the MR scanner.

Any arrangement of guidewire contacts described herein or known to one of skill in the art may be deployed within a contact carrier (702) of the combined connector (700). An interface circuit (710) may be arranged adjacent to the contact carrier (702) and within a common housing (712). The guidewire contacts are electrically coupled to the interface circuit using any type of electrical contact configuration, such as a coaxial connector, individual sliding or rotating contacts or hardwire connection.

Use of the combined connector may substantially diminish the risk of guidewire disconnection from the interface circuit during operation. This risk can be troublesome because the guidewire antenna can cause RF heating of the tissue surrounding it if not appropriately connected to the interface circuit during use, e.g., the transmit cycle of the MR imaging sequence.

To guard further against unintentional disconnection of the guidewire from the interface circuit, the connector may further include a connection detector. The connection detector may be exposed to the channel. The detector circuit may couple with at least one of the contacts in the connector. The detector circuit can couple with a standalone detector. The detector circuit may cause an alarm to be tripped in order to notify an operator or technician that a disconnection has occurred. The detector circuit may also couple with the MRI systems control signals to, e.g., notify the user and/or terminate the scan in case of a disconnect from the system.

An example of a connection detector can be a pair of contacts that form a closed circuit when they touch one or more of the guidewire contacts. The closed circuit could power an LED display, alarm, or indicator. Such a display, alarm, or indicator can provide constant reassurance to the operator or control room technician that the guidewire is connected, or could notify the operator or technician that disconnection has occurred. The closed circuit could also function as an interlock with the MRI system supplied control signals.

Figure 12:
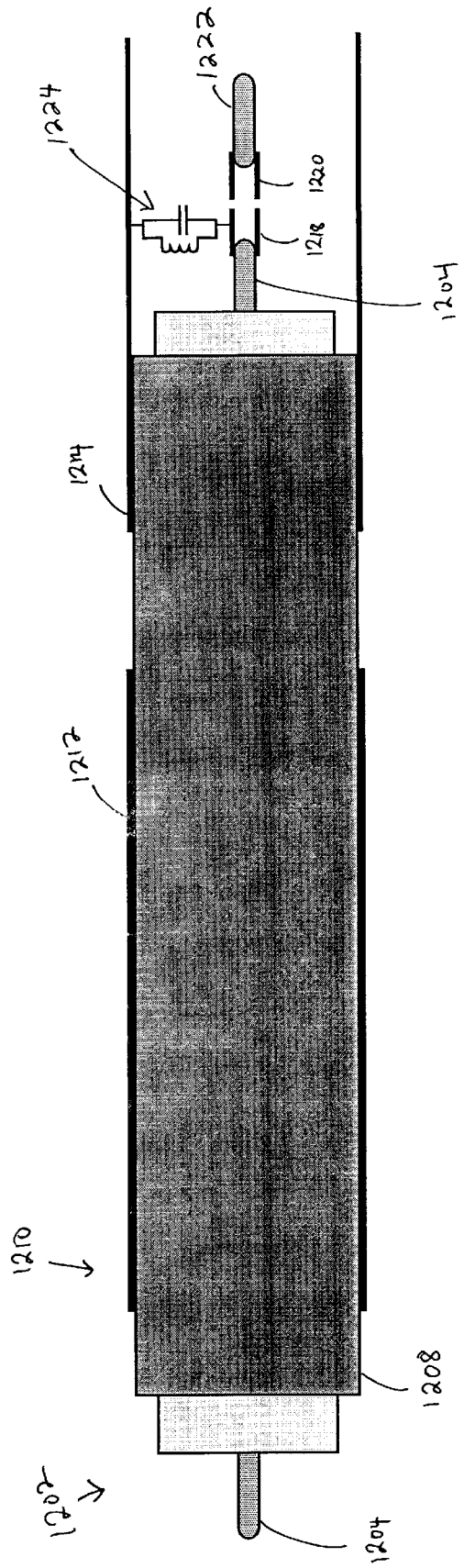
FIG. 12 shows an embodiment of a connector having a connection detector.

In an embodiment shown in FIG. 12, the proximal end of the guidewire (1202) having an inner conductor (1204) and outer conductor (1208) can be inserted into the distal end of the connector (1210). As the guidewire (1202) can be advanced through the connector, the outer conductor (1208) can bridge the gap between distal and proximal connector contacts (1212, 1214). The inner conductor (1204) can bridge the gap between distal and proximal inner contacts (1218, 1220). A control signal supplied from the system side on a center pin (1222) can thus be routed through a detector circuit, such as the capacitor/inductor combination (1224), onto the outer conductor (1208), and thence to the system.

Another example of a connection detector may be a mechanical switch deployed within the channel of the connector, into which the guidewire can be inserted. When fully inserted, the guidewire actuates this switch, closing a circuit or otherwise permitting transmission of a connection signal.

Another example of a connection detector contemplates the closure and/or securing of the guidewire within the connector to be contingent upon full insertion of the guidewire. A lever, cam, button, or other such device used to secure the guidewire in the connector may be arranged so that it can be actuated by a fully inserted guidewire, or that it can not be actuated unless the guidewire is fully inserted.

In another example, a light source can be positioned to emit light into the channel. A detector monitors the emitted light. In an embodiment, insertion of the guidewire obscures the light. The detector senses that the received light is diminished and thereby fails to send a disconnect signal. In another embodiment, the detector may send a connect signal as long as the guidewire is obscuring the emitted light.

In another example, a light source can be positioned to emit light into the channel. A detector monitors the emitted light. The emitted light is directed such that it is not received by the detector in the absence of a filly inserted guidewire. In an embodiment, insertion of the guidewire alters the emitted light path. In an embodiment, insertion of the guidewire causes the emitted light to be reflected or refracted so that it is received by the detector. The detector may send a connect signal when the guidewire is sufficiently inserted. The detector may send a disconnect signal when the guidewire is insufficiently inserted.

In another example, an activated LED may be positioned on one side of the channel, and a detector monitors the light emitted therefrom. Full insertion of a guidewire could obstruct the emitted light path or change the pattern of reflection and thereby permit detection of the insertion. In another example, the connector may be provided with source and detector optical fibers. Full insertion of the guidewire could create an imposition between the two fibers, disrupting reflection and facilitating detection of full guidewire insertion. In another example, the source fiber may conduct light from a light source external to the conductor.

In another example, an inductive or capacitive sensor may be integrated into the connector so that the presence of the guidewire can be detected.

Figure 13:
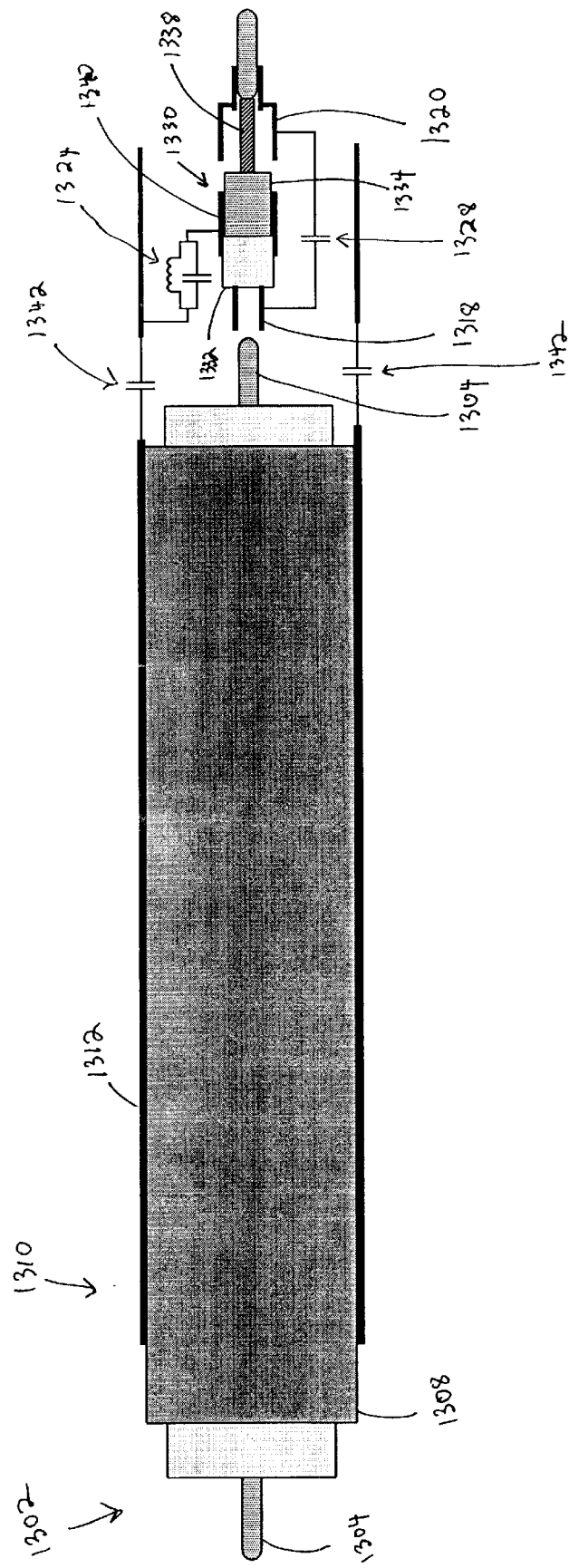
FIG. 13 shows an embodiment of a connector having a connection detector and a DC blocking circuit.

The connector may also include a DC blocking circuit. It may be combined with a connection detector. FIG. 13 depicts another embodiment of a connection detector combined with a DC blocking circuit. The proximal end of the guidewire (1302) having an inner conductor (1304) and outer conductor (1308) may be inserted into the distal end of the connector (1310). As the guidewire (1302) is advanced through the connector, the outer conductor (1308) can contact outer contact (1312). The inner conductor (1304) contacts a distal inner contact (1318) and may be electrically coupled to proximal inner contact (1320) through an RF bypass capacitor (1328). The inner conductor (1304) can make contact with a push button assembly (1330) having a distal insulating block (1332), a conductive midsection block (1334) and, e.g., a proximal element (1338) that may be, e.g., a spring. As the inner conductor (1308) pushes the push button assembly (1330) toward the proximal end of the connector (1310), contact may be made between a detection contact (1340) coupled to detector circuit (1324) and the proximal inner contact (1320). This completes a DC path for the control signals from the MR system through the detector circuit (1324). DC voltage can be blocked from the outer conductor (1308) by the RF bypass capacitors (1342).

The connector may also include an identification system. The identification could help ensure that the proper guidewire and connector combination is being used. In an embodiment, the identification system includes a predefined size and/or shape of the orifice of the connector. This predetermined size and/or shape could be selected to allow insertion and/or secure attachment of only appropriately configured guidewires. In an embodiment, the identification system could include a guidewire sensor that recognizes electrically or electronically encoded parameters in the guidewire, such as resistor values, digital signatures, unique serial numbers, or barcodes printed on the guidewires that may be scanned before use or read during insertion of the guidewire. This could help ensure proper combinations of guidewires and connectors and could also help ensure, if desired, that a particular guidewire, having a unique serial number, is used only one time.

Although certain embodiments of these systems and methods are disclosed herein, it should be understood that other embodiments are envisioned as would be understood by one of ordinary skill in the art. The specific embodiments described herein are provided for illustrative purposes. It is not intended that the invention be limited to those specific embodiments. Rather, it is intended that all variations and modifications as fall within the spirit of the invention be included within the scope.

We claim:

1. A connector for receiving an MRI guidewire, comprising:
    an orifice for receiving an end of said guidewire;
    a channel communicating with said orifice and providing an insertion path for said end of said guidewire;
    a first contact at least partly exposed to said channel, said first contact sized and shaped to couple with an inner conductor contact of said guidewire;

a second contact at least partly exposed to said channel, said second contact sized and shaped to couple with an outer conductor contact of said guidewire, said first and second contacts being sequentially disposed along said insertion path;

an output terminal electrically coupled to said first and second contacts; and a fastener structured and positioned to hold said end of said guidewire within said channel.

2. The connector of claim 1, wherein said first contact comprises a collet.

3. The connector of claim 1, wherein said first contact comprises a tubular contact.

4. The connector of claim 1, wherein said first contact comprises a formed metal contact.

5. The connector of claim 4, wherein a portion of said formed metal contact is oriented tangentially with respect to said channel.

6. The connector of claim 1, wherein said first contact comprises a wire.

7. The connector of claim 1, wherein said first contact comprises a tubular mesh.

8. The connector of claim 1, wherein said first contact comprises a metal ring.

9. The connector of claim 1, wherein said first contact comprises a spring.

10. The connector of claim 9, wherein said spring is deformed on its perimeter.

11. The connector of claim 9, wherein said spring is longitudinally deformed.

12. The connector of claim 1 structured for repeated removal from and reattachment to said guidewire.

13. The connector of claim 1, wherein said first contact extends axially to said output terminal to form said center pin.

14. The connector of claim 1, wherein said first contact comprises a spring piston.

15. The connector of claim 1, wherein said second contact comprises a collet.

16. The connector of claim 1, wherein said second contact comprises a tubular contact.

17. The connector of claim 1, wherein said second contact comprises a formed metal contact.

18. The connector of claim 17, wherein a portion of said formed metal contact is oriented tangentially with respect to said channel.

19. The connector of claim 1, wherein said second contact comprises a wire.

20. The connector of claim 1, wherein said second contact comprises a tubular mesh.

21. The connector of claim 1, wherein said second contact comprises a metal ring.

22. The connector of claim 1, wherein said second contact comprises a spring.

23. The connector of claim 22, wherein said spring is deformed on its perimeter.

24. The connector of claim 22, wherein said spring is longitudinally deformed.

25. The connector of claim 1, wherein said orifice is sized and shaped to permit insertion of a preselected type of said guidewire.

26. The connector of claim 1, wherein said second contact extends axially to said output terminal to form said center pin.

27. The connector of claim 1, wherein said second contact comprises a spring piston.

28. The connector of claim 1, wherein said inner conductor contact extends axially to said output terminal to form said center pin.

29. The connector of claim 1, further comprising a cap screwably attachable to said connector.

30. The connector of claim 29, further comprising a wiper disposed in said cap, said wiper shaped and positioned to contact said guidewire while said connector is receiving said guidewire.

31. The connector of claim 1, further comprising a wiper shaped and positioned to contact said guidewire while said connector is receiving said guidewire.

32. The connector of claim 1, further comprising a contact carrier surrounding said channel.

33. The connector of claim 32, wherein said carrier is rotatable with respect to said connector.

34. The connector of claim 32, wherein said guidewire is rotatably fixed with respect to said carrier.

35. The connector of claim 32, further comprising a wedge disposed between said orifice and said carrier.

36. The connector of claim 35, further comprising a spring disposed between said wedge and said carrier.

37. The connector of claim 32, wherein said fastener couples to said carrier.

38. The connector of claim 1, wherein said fastener includes at least one of a cap, a lever, a button, a cam, a return spring, a detent, a collet, a snap, a dial, or threads.

39. The connector of claim 1, wherein said first contact is positioned proximal to said second contact with respect to said output terminal, and said second contact is positioned distal to said first contact.

40. The connector of claim 1, wherein said first contact is positioned distal to said second contact with respect to said output terminal, and said second contact is positioned proximal to said first contact.

41. The connector of claim 1, wherein said first contact and said second contact are electrically insulated from each other by an insulator.

42. The connector of claim 1, wherein said first contact and said second contact are physically isolated from each other.

43. The connector of claim 1, further comprising an interface circuit electrically coupled to said first and second contacts.

44. The connector of claim 43, wherein said interface circuit comprises a tuning/matching circuit.

45. The connector of claim 43, wherein said interface circuit comprises a decoupling circuit.

46. The connector of claim 43, wherein said interface circuit comprises a balun trap circuit.

47. The connector of claim 1, further comprising a connection detector exposed to said channel.

48. The connector of claim 47, wherein said detector circuit is coupled to an indicator, said indicator indicating whether said guidewire is sufficiently inserted into said channel.

49. The connector of claim 47, wherein said detector comprises a mechanical switch deployed in said channel, wherein said switch is actuated by said guidewire when said guidewire is sufficiently inserted into said channel.

50. The connector of claim 47, wherein said detector comprises a pair of contacts, wherein a closed circuit is formed between said pair of contacts when said guidewire is sufficiently inserted into said channel.

51. The connector of claim 47, wherein said detector comprises a light source and a light detector disposed in said channel, and wherein insertion of said guidewire alters the path of light emitted from said light source when said guidewire is sufficiently inserted into said channel.

52. The connector of claim 51, wherein insertion of said guidewire reflects said light onto said light detector.

53. The connector of claim 51, wherein insertion of said guidewire reflects said light away from said light detector.

54. The connector of claim 51, wherein said source comprises a light emitting diode.

55. The connector of claim 51, wherein said source comprises an optical fiber.

56. The connector of claim 47, wherein said detector circuit sends a connect signal when said guidewire is sufficiently inserted.

57. The connector of claim 47, wherein said detector circuit send a disconnect signal when said guidewire is insufficiently inserted.

58. The connector of claim 47, wherein said detector comprises at least one of an inductive sensor and a capacitive sensor, wherein said detector detects the presence of said guidewire in said channel.

59. The connector of claim 47, wherein said detector circuit causes an alarm to be tripped when said guidewire is insufficiently inserted into said connector.

60. The connector of claim 47, wherein said detector circuit causes an MRI scan to be terminated when said guidewire is insufficiently inserted into said connector.

61. The connector of claim 41, wherein said connector further comprises an identification system, and wherein said identification system recognizes a parameter of said guidewire.

62. The connector of claim 1, further comprising a DC blocking capacitor electrically coupled to at least one of said first and second contacts.

63. The connector of claim 62, further comprising an RF bypass capacitor electrically coupled to at least one of said first and second contacts.

64. The connector of claim 1, wherein said connector is formed of MR-compatible materials.

65. The connector of claim 1, wherein said connector is formed of biocompatible materials.

66. A connector for receiving an MRI guidewire, comprising:
   an orifice for receiving an end of said guidewire;
   a channel communicating with said orifice and providing an insertion path for said end of said guidewire;
   a first contact at least partly exposed to said channel, said first contact sized and shaped to couple with an inner conductor contact of said guidewire;
   a second contact at least partly exposed to said channel, said second contact sized and shaped to couple with an outer conductor contact of said guidewire, said first and second contacts being sequentially disposed along said insertion path;
   an output terminal electrically coupled to said first and second contacts;
   an interface circuit electrically coupled to said first and second contacts; and
   a fastener structured and positioned to hold said end of said guidewire within said channel.

67. A connector for receiving an MRI guidewire, comprising:
   an orifice for receiving an end of said guidewire;
   a channel communicating with said orifice and providing an insertion path for said end of said guidewire;
   a first contact at least partly exposed to said channel, said first contact sized and shaped to couple with an inner conductor contact of said guidewire;
   a second contact at least partly exposed to said channel, said second contact sized and shaped to couple with an outer conductor contact of said guidewire, said first and second contacts being sequentially disposed along said insertion path;
   an output terminal electrically coupled to said first and second contacts;
   a connection detector exposed to said channel; and
   a fastener structured and positioned to hold said end of said guidewire within said channel.

68. A connector for receiving an MRI guidewire, comprising:
   an orifice for receiving an end of said guidewire;
   a channel communicating with said orifice and providing an insertion path for said end of said guidewire;
   a first contact at least partly exposed to said channel, said first contact sized and shaped to couple with an inner conductor contact of said guidewire;
   a second contact at least partly exposed to said channel, said second contact sized and shaped to couple with an outer conductor contact of said guidewire, said first and second contacts being sequentially disposed along said insertion path;
   an output terminal electrically coupled to said first and second contacts;
   a DC blocking capacitor electrically coupled to at least one of said first and second contacts; and
   a fastener structured and positioned to hold said end of said guidewire within said channel.

69. A connector for receiving an MRI guidewire, comprising:
   an orifice for receiving an end of said guidewire;
   a channel communicating with said orifice and providing an insertion path for said end of said guidewire;
   a first contact at least partly exposed to said channel, said first contact sized and shaped to couple with an inner conductor contact of said guidewire;
   a second contact at least partly exposed to said channel, said second contact sized and shaped to couple with an outer conductor contact of said guidewire, said first and second contacts being sequentially disposed along said insertion path;
   an output terminal electrically coupled to said first and second contacts;
   an interface circuit electrically coupled to said first and second contacts;
   a connection detector exposed to said channel; and
   a fastener structured and positioned to hold said end of said guidewire within said channel.

70. A connector for receiving an MRI guidewire, comprising:
   an orifice for receiving an end of said guidewire;
   a channel communicating with said orifice and providing an insertion path for said end of said guidewire;
   a first contact at least partly exposed to said channel, said first contact sized and shaped to couple with an inner conductor contact of said guidewire;
   a second contact at least partly exposed to said channel, said second contact sized and shaped to couple with an outer conductor contact of said guidewire, said first and second contacts being sequentially disposed along said insertion path;
   an output terminal electrically coupled to said first and second contacts;
   an interface circuit electrically coupled to said first and second contacts;

a connection detector exposed to said channel;

a DC blocking capacitor electrically coupled to at least one of said first and second contacts; and a fastener structured and positioned to hold said end of said guidewire within said channel.

71. A medical device, comprising:

a magnetic resonance imaging (MRI) guidewire, comprising:
  an inner conductor;
  an outer conductor coaxially disposed about said inner conductor;
  a distal end sized and shaped for insertion into a subject to receive MRI signals; and
  a proximal end sized and shaped for insertion into a connector, said proximal end having
    an outer conductor contact coupled electrically to said outer conductor, and an extended section of said inner conductor that extends axially beyond said outer conductor contact, said extended section including:
      an inner conductor contact having an electrically conductive material disposed at least partially around said inner conductor; and
      an insulated area interposed between said outer conductive contact and said inner conductive contact, and having an electrically insulating material disposed at least partially around said inner conductor; and a connector for receiving said MRI guidewire, comprising:
  an orifice for receiving said proximal end of said guidewire;
  a channel communicating with said orifice and providing an insertion path for said proximal end of said guidewire;
  a first contact at least partly exposed to said channel, said first contact sized and shaped to couple with said inner conductor contact of said guidewire;
  a second contact at least partly exposed to said channel, said second contact sized and shaped to couple with said outer conductor contact of said guidewire, said first and second contacts being sequentially disposed along said insertion path;
  an output terminal electrically coupled to said first and second contacts; and
  a fastener structured and positioned to hold said proximal end of said guidewire within said channel.

72. The medical device of claim 71, wherein the diameter of said guidewire is sized for insertion into the lumen of an anatomic structure of a subject.

73. The medical device of claim 72, wherein said anatomic structure is a blood vessel.

74. The medical device of claim 72, wherein said subject is a human.

75. The medical device of claim 71, wherein the guidewire diameter is less than about 0.040 inches.

76. The medical device of claim 75, wherein said diameter is between about 0.012 inches and 0.038 inches.

77. The medical device of claim 76, wherein said diameter is about 0.014 inches.

78. The medical device of claim 71, wherein a diameter of said inner conductor is between about 0.004 inches and about 0.012 inches.

79. The medical device of claim 71, wherein said guidewire has a stiffness sufficient for insertion into a lumen of an anatomic structure of a subject.

80. The medical device of claim 71, wherein said guidewire is biocompatible.

81. The medical device of claim 71, wherein said guidewire comprises a conductive material.

82. The medical device of claim 71, wherein said guidewire is composed of nonmagnetic materials.

83. The medical device of claim 71, wherein said guidewire comprises a superelastic material.

84. The medical device of claim 83, wherein said superelastic material comprises titanium.

85. The medical device of claim 83, wherein said superelastic material comprises Nitinol.

86. The medical device of claim 71, wherein said guidewire is sterilizable.

87. The medical device of claim 71, wherein said outer conductor contact and said inner conductor contact are each annular in shape.

88. The medical device of claim 87, wherein said outer conductor contact and said inner conductor contact have approximately equal diameters.

89. The medical device of claim 87, wherein said inner conductor contact is disposed radially about a portion of said extended section of said inner conductor.

90. The medical device of claim 71, wherein said insulated area is annular in shape.

91. The medical device of claim 71, wherein said outer conductor contact is axially distal to said inner conductor contact.

92. The medical device of claim 71, further comprising an extension attachment coupled to said proximal end of said guidewire.

93. The medical device of claim 71, further comprising an identification parameter.

94. The medical device of claim 93, wherein said identification parameter comprises at least one of a resistor value, a digital signature, or a unique serial number.

* * * * *